US006562781B1

(12) United States Patent
Berry et al.

(10) Patent No.: US 6,562,781 B1
(45) Date of Patent: May 13, 2003

(54) GLYCOSAMINOGLYCAN-ANTITHROMBIN III/HEPARIN COFACTOR II CONJUGATES

(75) Inventors: Leslie Berry, Burlington (CA); Maureen Andrew, Oakville (CA)

(73) Assignee: Hamilton Civic Hospitals Research Development Inc., Ontario (CA)

( * ) Notice: Subject to any disclaimer, the term of this patent is extended or adjusted under 35 U.S.C. 154(b) by 0 days.

(21) Appl. No.: 08/564,976

(22) Filed: Nov. 30, 1995

(51) Int. Cl.[7] .................. C07K 14/435; A61K 38/16

(52) U.S. Cl. ................. 514/2; 530/350; 530/395; 536/21

(58) Field of Search .................. 530/300, 330, 530/393; 536/21; 260/123.7; 514/2, 21; 435/405

(56) References Cited

U.S. PATENT DOCUMENTS

| | | |
|---|---|---|
| 2,824,092 A | 2/1958 | Thompson |
| 3,616,935 A | 11/1971 | Love et al. |
| 3,673,612 A | 7/1972 | Merrill et al. |
| 3,842,061 A | 10/1974 | Andersson et al. |
| 4,055,635 A | 10/1977 | Green et al. |
| 4,213,962 A | 7/1980 | Miura et al. |
| 4,301,153 A | 11/1981 | Rosenberg |
| 4,340,589 A | 7/1982 | Uemura et al. |
| 4,356,170 A | 10/1982 | Jennings et al. |
| 4,446,126 A | 5/1984 | Jordan |
| 4,448,718 A * | 5/1984 | Yannas et al. ........... 260/123.7 |
| 4,465,623 A | 8/1984 | Chanas et al. |
| 4,496,550 A | 1/1985 | Lindahl et al. |
| 4,510,084 A | 4/1985 | Eibl et al. |
| 4,526,714 A | 7/1985 | Feijen et al. |
| 4,585,754 A | 4/1986 | Meisner et al. |
| 4,613,665 A | 9/1986 | Larm |
| 4,623,718 A * | 11/1986 | Collen ........................ 530/393 |
| 4,656,161 A | 4/1987 | Herr |
| 4,689,323 A | 8/1987 | Mitra et al. .................... 514/56 |
| 4,731,073 A | 3/1988 | Robinson |
| 4,745,180 A * | 5/1988 | Moreland et al. ........... 530/350 |
| 4,863,907 A | 9/1989 | Sakurai et al. |
| 4,920,194 A | 4/1990 | Feller et al. |
| 4,935,204 A | 6/1990 | Seidel et al. |
| 4,987,181 A | 1/1991 | Bichon et al. |
| 5,002,582 A | 3/1991 | Guire et al. |
| 5,023,078 A * | 6/1991 | Halluin ..................... 424/94.64 |
| 5,061,750 A | 10/1991 | Feijen et al. |
| 5,071,973 A | 12/1991 | Keller et al. |
| 5,084,273 A | 1/1992 | Hirahara |
| 5,134,192 A | 7/1992 | Feijen et al. |
| 5,159,050 A | 10/1992 | Onwumere |
| 5,171,264 A | 12/1992 | Merrill |
| 5,182,259 A | 1/1993 | Kita |
| 5,182,317 A | 1/1993 | Winters et al. |
| 5,222,971 A | 6/1993 | Willard et al. |
| 5,262,451 A | 11/1993 | Winters et al. |
| 5,270,046 A | 12/1993 | Sakamoto et al. |
| 5,275,838 A | 1/1994 | Merrill |
| 5,308,617 A * | 5/1994 | Halluin ..................... 424/94.64 |
| 5,310,881 A | 5/1994 | Sakurai et al. |
| 5,319,072 A | 6/1994 | Uemura et al. |
| 5,330,907 A | 7/1994 | Philapitsch et al. |
| 5,338,770 A | 8/1994 | Winters et al. |
| 5,364,350 A | 11/1994 | Dittmann |
| 5,436,291 A | 7/1995 | Levy et al. |
| 5,455,040 A | 10/1995 | Marchant |
| 5,529,986 A | 6/1996 | Larsson et al. |
| 5,589,516 A | 12/1996 | Uriyu et al. |
| 5,652,014 A | 7/1997 | Galin et al. |
| 5,741,852 A | 4/1998 | Marchant et al. |
| 5,741,881 A | 4/1998 | Patnaik |
| 5,762,944 A | 6/1998 | Inoue et al. |
| 5,782,908 A | 7/1998 | Cahalan et al. |
| 5,843,172 A | 12/1998 | Yan |
| 5,851,229 A | 12/1998 | Lentz et al. |
| 5,855,618 A | 1/1999 | Patnaik et al. |
| 5,866,113 A | 2/1999 | Hendriks et al. |
| 5,876,433 A | 3/1999 | Lunn |
| 5,879,697 A | 3/1999 | Ding et al. |
| 5,891,196 A | 4/1999 | Lee et al. |
| 5,944,753 A | 8/1999 | Galin et al. |
| 5,945,457 A | 8/1999 | Plate et al. |
| 5,955,438 A | 9/1999 | Pitaru et al. |
| 6,024,918 A | 2/2000 | Hendriks et al. |
| 2001/0007063 A1 | 7/2001 | Yoshihiro et al. |
| 2001/0034336 A1 | 10/2001 | Shah et al. |

FOREIGN PATENT DOCUMENTS

| | | |
|---|---|---|
| EP | 0 081 853 | 6/1983 |
| EP | 0 098 814 | 1/1984 |
| EP | 0 137 356 | 4/1985 |
| EP | 0 344 068 | 11/1989 |
| EP | 0 345 616 | 12/1989 |
| FR | 2 635 019 | 2/1990 |
| WO | 89/09624 | 10/1989 |
| WO | 90/01332 | 2/1990 |
| WO | 9505400 * | 2/1995 |

OTHER PUBLICATIONS

Berry et al. (1998) J. Biochem. 124: 434–439.*

I. Bjork, et al., *Permanent Activation of Antithrombin by Covalent Attachment of Heparin Oligosaccharides* FEBS Letters, vol. 143, 96–100 (1982).

R. Ceustermans, et al., *Preparation, Characterization, and Turnover Properties of Heparin–Antithrombin III Complexes Stabilized by Covalent Bonds*  The Journal of Biological Chemistry, vol. 257, 3401–3408 (1982).

(List continued on next page.)

*Primary Examiner*—Michael Pak
(74) *Attorney, Agent, or Firm*—Millen, White, Zelano & Branigan, P.C.

(57) ABSTRACT

Novel conjugates of glycosaminoglycans, particularly heparin and dermatan sulfate, and amine containing species and therapeutic uses thereof are described. In particular, mild methods of conjugating heparins to proteins, such as antithrombin III and heparin cofactor II, which provide covalent conjugates which retain maximal biological activity are described. Uses of these conjugates to prevent thrombogenesis, in particular in lung airways, such as found in infant and adult respiratory distress syndrome are also described.

49 Claims, 8 Drawing Sheets

OTHER PUBLICATIONS

M.W.C. Hatton, et al., *Tritiation of Commericial Heparins by Reaction with NaB³H₄: Chemical Analysis and Biological Properties of the Product Analytical Biochemistry*, vol. 106, 417–426 (1980).

M. Hoylaerts, et al., *Covalent Complexes Between Low Molecular Weight Heparin Fragments and Antithrombin III–Inhibition Kinetics and Turnover Parameters Thromb Haemostas*, vol. 49, 109–115 (1983).

M. Hoylaerts, et al., *Involvement of Heparin Chain Length in the Heparin–catalyzed Inhibition of Thrombin by Antithrombin III\* The Journal of Biological Chemistry*, vol. 259, 5670–5677 (1984).

C. Mattsson, et al., *Antithrombotic Properties in Rabbits of Heparin and Heparin Fragments Covalently Coupled to Human Antithrombin III J. Clin. Invest.*, vol. 75, 1169–1173 (1985).

Maimone, M.M., et al., "Structure of a Dermatan Sulfate Hexasaccharide That Binds to Heparin Cofactor Cofactor II With High Affinity," *J. of Bio. Chem.*, vol. 265, No. 30, pp. 18263–18271 (1990).

Uno, Takeji, et al., "Evaluation for antithrombogenicity on the surface of heparinized biomedical material using thrombin–antithrombin III complex," *Chemical Abstracts*, vol. 122, No. 25, Abstract No. 306176 (Jun. 19, 1995).

Hatton, M.W.C., et al., "Inhibition of Thrombin by Antithrombin III in the Presence of Certain Glycosaminoglycans Found in the Mammalian Aorta," *Thrombosis Research*, 13:4, 655–670 (Apr. 24, 1978).

Verstraete, M., "Prevention of Thrombosis in Arteries: Novel Approaches," *J. Cardiovasc. Pharmacol.*, 7 (Suppl. 3) S191–S205 (1985).

Radoff, et al., *Radioreceptor Assay for Advanced Glycosylation End Products*, Diabetes, vol. 40, pp. 1731–1738, Dec. 1991.

Axen, Rolf et al., "Chemical Fixation of Enzymes to Cyanogen Halide Activated Polysaccharide Carriers," *Eur. J. Biochem.*, vol. 18, pp. 351–360 (1971).

Kohn, Joachim et al., "A new approach (cyano–transfer) for cyanogen bromide activation of sepharose at Neutral pH, which yields activated resins, free of interfering nitrogen derivatives," *Biochemical and Biophysical Research Communications*, vol. 107, No. 3, pp. 878–884, (1982).

*Pharmacology*, vol. 103, p. 45 (1985) Missing Author.

The 2nd Rokko Conference (with translation) Missing Author, Date, Ref Info.

Takuya Fujuita et al., "Alteration of biopharmaceutical properties of drugs by their conjugation with water–soluble macromolecules: uricase–dextran conjugate," *Journal of Controlled Release*, vol. 11, pp. 149–156 (1990).

Te Piao King et al., "Immunochemical studies of dextran coupled ragweed pollen allergen, antigen $E^1$," *Archives of Biochemistry and Biophysics*, pp. 464–473 (1975).

Fu–Tong Liu et al., "Immunological tolerance to allergenic protein determinants: A therapeutic approach for selective inhibition of IgE antibody production," *Proc. Natl., Acad. Sci. USA*, vol. 76, No. 3, pp. 1430–1434 (1979).

Hiroshi Maeda et al., "Conjugation of Poly(styrene–co–maleic acid) derivatives to the antitumor protein neocarzinostatin: pronounced improvements in pharmacological properties," *J. Med. Chem.*, vol. 28, pp. 455–461 (1985).

M. Okada et al., "Suppression of IgE antibody responses against ovalbumin by the chemical conjugate of ovalbumin with a polyaspartic acid derivative," *Int. Archs Allergy appl. Immun.*, vol. 76, pp. 79–81 (1985).

Mitsuko Usui et al., "IgE–selective and antigen–specific unresponsiveness in mice," *The Journal of Immunology*, vol. 122, No. 4, pp. 1266–1272 (1979).

\* cited by examiner

GLYCOSAMINOGLYCAN-ANTITHROMBIN III/HEPARIN COFACTOR II CONJUGATES

BACKGROUND OF THE INVENTION

1. Field of the Invention

This invention relates to new chemical compounds comprising covalent conjugates of glycosaminoglycans, particularly heparins, methods for their preparation, their pharmaceutical compositions and therapeutic uses thereof.

2. Description of the Background Art

Heparin is a sulfated polysaccharide which consists largely of an alternating sequence of hexuronic acid and 2-amino-2-deoxy-D-glucose. Heparin and a related compound, dermatan sulfate, are of great importance as anticoagulants for clinical use in the prevention of thrombosis and related diseases. They are members of the family of glycosaminoglycans, (GAGs), which are linear chains of sulfated repeating disaccharide units containing a hexosamine and a uronic acid. Anticoagulation using GAGs (such as heparin and dermatan sulfate) proceeds via their catalysis of inhibition of coagulant enzymes (the critical one being thrombin) by serine protease inhibitors (serpins) such as antithrombin III (ATIII) and heparin cofactor II (HCII). Binding of the serpins by the catalysts is critical for their action and occurs through specific sequences along the linear carbohydrate chain of the glycosaminoglycan (GAG). Heparin acts by binding to ATIII via a pentasaccharide sequence, thus potentiating inhibition of a variety of coagulant enzymes (in the case of thrombin, heparin must also bind to the enzyme). Heparin can also potentiate inhibition of thrombin by binding to the serpin HCII. Dermatan sulfate acts by specifically binding to HCII via a hexasaccharide sequence, thus potentiating only the inhibition of thrombin. Since glycosaminoglycans (particularly heparin) can bind to other molecules in vivo or be lost from the site of action due to a variety of mechanisms, it would be advantageous to keep the GAG permanently associated with the serpin by a covalent bond.

Covalent complexes between ATIII and heparin have been produced previously; see, e.g., Bjork et al., (1982) *FEBS Letters* 143(1):96–100, and by Collen et al., U.S. Pat. No. 4,623,718. These conjugates required covalent modification of the heparin prior to its conjugation. The product by Bjork et al. (produced by reduction of the Schiff base between the aldehyde of a 2,5-D-anhydromannose terminus of heparin, produced by partial depolymerization of heparin to heparin fragments with nitrous acid, and a lysyl amino of ATIII) had undetectable antithrombin activity. The product by Collen et al. (produced by conjugation of carboxyl groups within the chain of the heparin molecule and lysyl amino groups of ATIII through amino-hexyl tolyl spacer arms) had a random attachment to the carboxyls of the uronic acids of the heparin moiety that might affect the ATIII binding sequence and in fact the specific anti-Xa (a coagulation protease which activates prothrombin to thrombin) activity was approximately 65% of the starting non-covalently linked unmodified heparin (*J. Biol. Chem.* 257:3401–3408 (1982)). The specific anti-thrombin activity would also be, therefore, 65% or less since both Xa and thrombin require heparin binding to ATIII. The bimolecular rate constant of the product by Collen et al. for inhibition of thrombin was claimed to be comparable to that of non-covalent mixtures of heparin saturated with ATIII (*J. Biol. Chem.* 259:5670–5677 (1984)). However, large molar excesses of heparin or covalent complex over thrombin (>10:1) were used to simplify the kinetics, which would mask the effect of any subpopulation of molecules with low activity. Specific antithrombin activities were not given.

In addition, heparin has also been covalently conjugated to other proteins (such as tissue plasminogen activator and erythropoietin) by Halluin (U.S. Pat. No. 5,308,617), using a similar method to that of Bjork et al. These conjugates suffered from the same problems associated with loss of heparin activity as with the Bjork conjugates. Coupling of heparin to affinity supports via a hydrazine linkage is reported in WO 95/05400. However, the hydrazine group is not commonly found in proteins and other macromolecules, and its incorporation often results in a decrease in biological activity. U.S. Pat. No. 4,213,962 describes heparin and antithrombin III coimmobilized on cyanogen bromide activated agarose. U.S. Pat. Nos. 5,280,016 and 4,990,502 describe the oxidation of heparin with periodate and reduction of the aldehydes so generated.

Therefore, it would be desirable to provide covalent conjugates of heparin and related glycosaminoglycans which retain maximal biological activity (e.g., anticoagulant activity) and improved pharmacokinetic properties and simple methods for their preparation. This invention fulfills these and other needs.

SUMMARY OF THE INVENTION

This invention provides a covalent conjugate comprising a glycosaminoglycan linked to another species by a covalent linkage wherein the species comprises at least one primary amino group, wherein the species is directly covalently linked via its amino group to a terminal aldose residue of the glycosaminoglycan. Preferably, the covalent linkage is an imine (>C=N—) formed between the amino group of the first species and the C1 of the terminal aldose, or the amine reduction product thereof (>CH—NH—). The glycosaminoglycan is preferably heparin or dermatan sulfate. The amine containing species may be a small molecule, such as a drug or a label, a macromolecule such as antithrombin III or heparin cofactor II, or a solid or porous or semiporous support such as is typically used in affinity chromatography.

The invention also provides novel and mild methods of preparing the above covalent conjugates which retain maximal biological activity. The methods comprise incubating the glycosaminoglycans with the amine-containing species under conditions which allow imine formation between the terminal aldose residue of the glycosaminoglycan and the amine. The imine may be reduced to the corresponding amine or alternatively may be allowed to rearrange under mild conditions (Amadori rearrangement) to an α-carbonyl amine. The invention further provides pharmaceutical compositions comprising these conjugates and therapeutic uses thereof.

This invention provides novel covalent conjugates of glycosaminoglycans labelled at their terminal aldose residue with primary amine containing molecules. In particular, this invention provides novel covalent conjugates of heparin (Merck Index, 1980), dermatan sulfate (Tollefsen et al. (1990) *J. Biol. Chem.* 265:18263–18271) and fragments thereof with therapeutically significant serine protease inhibitors such as, for example, antithrombin III and heparin cofactor II, therapeutic uses thereof and methods for their preparation. The novel heparin conjugates of this invention are prepared under mild conditions, retain maximal anticoagulant activity compared to intact heparin, and have improved pharmacokinetic properties.

Before describing the invention in greater detail the following definitions are set forth to illustrate and define the meaning and scope of the terms used to describe the invention herein.

The term "hexose" refers to a carbohydrate ($C_6H_{12}O_6$) with six carbon atoms. Hexoses may be aldohexoses such as, for example, glucose, mannose, galactose, idose, gulose, talose, allose and altrose, whose open chain form contains an aldehyde group. Alternatively, hexoses may be ketoses such as fructose, sorbose, allulose and tagatose, whose open chain form contains a ketone group.

The term "uronic acid" refers to the carboxylic acid formed by oxidation of the primary hydroxyl group of a carbohydrate and are typically named after the carbohydrate from which they are derived. Therefore, oxidation of the C6 hydroxyl of glucose gives glucuronic acid, oxidation of the C6 hydroxyl of galactose gives galacturonic acid and oxidation of the C6 hydroxyl of idose gives iduronic acid.

The term "hexosamine" refers to a hexose derivative in which at least one hydroxy group, typically the C2 hydroxy group, has been replaced by an amine. The amine may be optionally alkylated, acylated (such as with muramic acid), typically by an acetyl group, sulfonated, (O or N-sulfated), sulfonylated, phosphorylated, phosphonylated and the like. Representative examples of hexosamines include glucosamine, galactosamine, tagatosamine, fructosamine, their modified analogs and the like.

The term "glycosaminoglycan" refers to linear chains of largely repeating disaccharide units containing a hexosamine and a uronic acid. The precise identity of the hexosamine and uronic acid may vary widely and representative examples of each are provided in the definitions above. The disaccharide may be optionally modified by alkylation, acylation, sulfonation (O— or N-sulfated), sulfonylation, phosphorylation, phosphonylation and the like. The degree of such modification can vary and may be on a hydroxy group or an amino group. Most usually the C6 hydroxyl and the C2 amine are sulfated. The length of the chain may vary and the glycosaminoglycan may have a molecular weight of greater than 200,000 daltons, typically up to 100,000 daltons, and more typically less than 50,000 daltons. Glycosaminoglycans are typically found as mucopolysaccharides. Representative examples include, heparin, dermatan sulfate, heparan sulfate, chondroitin-6-sulfate, chondroitin-4-sulfate, keratan sulfate, chondroitin, hyaluronic acid, polymers containing N-acetyl monosaccharides (such as N-acetyl neuraminic acid, N-acetyl glucosamine, N-acetyl galactosamine, and N-acetyl muramic acid) and the like and gums such as gum arabic, gum Tragacanth and the like. See Heinegard, D. and Sommarin Y. (1987) *Methods in Enzymology* 144:319–373.

The term "directly covalently linked" refers to a covalent linkage between two species accomplished without the use of intermediate spacer or linkage units. Thus, when a first molecule is referred to as being directly covalently linked to a terminal aldose residue of a glycosaminoglycan via an amino group on the first molecule, this means that the nitrogen atom of the first molecule is bonded directly to an atom of the terminal aldose residue. This bond will be a covalent bond and may be a single, double or triple bond. Therefore, one of skill in the art will understand that heparin conjugates linked to another molecule via initial attachment of spacer groups such as polymethylene diamino linkers to the heparin molecule are not contemplated by this invention.

The term "protein" includes, but is not limited to, albumins, globulins (e.g., immunoglobulins), histones, lectins, protamines, prolamines, glutelins, phospholipases, antibiotic proteins and scleroproteins, as well as conjugated proteins such as phosphoproteins, chromoproteins, lipoproteins, glycoproteins, nucleoproteins.

The term "serpin" refers to a serine protease inhibitor and is exemplified by species such as antithrombin III and heparin cofactor II.

The term "amine" refers to both primary amines, $RNH_2$, and secondary amines $RNH(R')$.

The term "amino" refers to the group >NH or —$NH_2$.

The term "imine" refers to the group >C=N— and salts thereof.

As used herein, the terms "treatment" or "treating" of a condition and/or a disease in a mammal, means:

(i) preventing the condition or disease, that is, avoiding any clinical symptoms of the disease;

(ii) inhibiting the condition or disease, that is, arresting the development or progression of clinical symptoms; and/or (iii) relieving the condition or disease, that is, causing the regression of clinical symptoms.

The conditions and diseases treated in the present invention include myocardial infarction and a large array of thrombotic states. These include fibrin deposition found in neonatal respiratory distress syndrome, adult respiratory distress syndrome, primary carcinoma of the lung, non-Hodgkins lymphoma, fibrosing alveolitis, and lung transplants. Also, the present invention can treat either acquired ATIII deficient states such as neonatal respiratory distress syndrome, L-asparaginase induced deficiency, cardiopulmonary bypass induced deficiency and sepsis or congenital ATIII deficient states. In the case of congenital ATIII deficiency, although it is unclear from the literature if any homozygous deficient infant has ever survived to the point of birth, life threatening thrombotic complications with ATIII levels of less than 0.25 Units/ml in heterozygotes requiring ATIII plus heparin may occur in up to 1 or 2 infants per year in the U.S.A.

Other uses of the invention include covalent coating of GAGs on amine containing surfaces such as central venous lines, cardiac catheterization, cardiopulmonary bypass circuits, dialysis circuits, or other external blood contacting instruments, as well as mechanical valves, stents or any in vivo prosthesis.

The novel compounds of this invention are prepared by a simple one step process, which provides for direct covalent attachment of the amine of an amine containing moiety (such as, but not limited to, amine containing oligo(poly) saccharides, amine containing lipids, proteins, nucleic acids and any amine containing xenobiotics) to a terminal aldose residue of a glycosaminoglycan. Preferably, the amine containing moiety is a protein possessing a desirable biological activity. The mild non-destructive methods provided herein allow for maximal retention of biological activity of the protein and allow direct linkage of the protein without the need for intermediate spacer groups as follows:

The glycosaminoglycan to be conjugated is incubated with the amine-containing species at a pH suitable for imine formation between the amine and the terminal aldose or ketose residue of the glycosaminoglycan. Terminal aldose and ketose residues generally exist as an equilibrium between the ring closed cyclic hemiacetal or hemiketal form and the corresponding ring opened aldehyde or ketone equivalents. Generally, amines are capable of reacting with the ring opened form to produce an imine (Schiff base). Typically, the aldoses are more reactive because the corresponding aldehydes of the ring open form are more reactive towards amines. Therefore, covalent conjugate formation between amines and terminal aldose residues of glycosaminoglycans provides a preferred method of attaching a species containing an amine to a glycosaminoglycan.

The reaction is typically carried out at a pH of about 4.5 to about 9, preferably at about 5 to about 8 and more preferably about 7 to about 8. The reaction is generally done in aqueous media. However, organic media, especially polar hydrophilic organic solvents such as alcohols, ethers and formamides and the like may be employed in proportions of up to about 40% to increase solubility of the reactants, if necessary. Non-nucleophilic buffers such as phosphate, acetate, bicarbonate and the like may also be employed.

Optionally and preferably, the imines formed by condensation of the amines of the first species with the terminal aldose residues of the glycosaminoglycans are reduced to the corresponding amines. This reduction may be accomplished concurrently with imine formation or subsequently. A wide array of reducing agents may be used, with hydride reducing agents, such as for example, sodium borohydride or sodium cyanoborohydride being preferred. Generally, any reducing agent that does not reduce disulfide bonds can be used.

Alternatively, if reduction of the intermediate imine is not desired, the imine may be incubated for a sufficient period of time, typically about 1 day to 1 month, more typically about 3 days to 2 weeks, to allow Amadori rearrangement of the intermediate imine. The terminal aldose residues of the glycosaminoglycans conjugated by the methods provided by this invention frequently possess C2 hydroxy groups on the terminal aldose residue, i.e., a 2-hydroxy carbonyl moiety which is converted to a 2-hydroxy imine by condensation with the amine of the species being conjugated to the glycosaminoglycan. In the Amadori rearrangement, which is particularly common in carbohydrates, the α-hydroxy imine (imine at C1, hydroxy at C2) formed by the initial condensation may rearrange to form an α-keto amine by enolization and re-protonation (keto at C2, amine at C1). The resulting α-carbonyl amine is thermodynamically favored over the precursor α-hydroxy imine, thus providing a stable adduct with minimal disruption of the glycosaminoglycan chain. Thus in this embodiment, the invention provides a glycosaminoglycan covalently conjugated at the C1 of the terminal aldose residue of the glycosaminoglycan to an amine containing species via an amine linkage. If desired, the resulting conjugate may be reduced or labelled by reduction of the C2 carbonyl group with a labelling reagent such a radiolabel (e.g., $NaB^3H_4$), see, M. W. C. Hatton, L. R. Berry et al. (1980) *Analytical Biochemistry* 106:417–426, or conjugated to a second amine containing species, such as a fluorescent label.

A variety of different amine containing species may be conjugated to the glycosaminoglycans by the methods disclosed herein. Therefore, this invention provides covalent conjugates of glycosaminoglycans and a variety of other species. The primary amine may be on a small molecule, such as, for example, a drug or fluorescent or chromophoric label or a macromolecule such as, for example, a protein (antibodies, enzymes, receptors, growth factors and the like), a polynucleotide (DNA, RNA and mixed polymers thereof) or a polysaccharide. Generally, when proteins are being conjugated to glycosaminoglycans, linkage will occur through the ε-amino groups of lysine residues. Alternatively, linkage may also be accomplished via the N-terminal amine by using a pH at which the ε-amino groups are protonated. In addition, many methods are known to one of skill in the art to introduce an amine functionality into a macromolecule, see, e.g., "Chemistry of Protein Conjugation and Crosslinking", by S. Wong (CRC Press, 1991) and "The Organic Chemistry of Biological Compounds", by Robert Barker (Prentice-Hall, 1971).

In particular, the present invention can be applied to a variety of other therapeutically useful proteins where longer half-life and blood coagulation considerations are important. These include blood enzymes, antibodies, hormones and the like as well as related plasminogen activators such as streptokinase and derivatives thereof. In particular, this invention provides conjugates of heparin or dermatan sulfate with antithrombin, heparin cofactor II or analogs of heparin cofactor II, described in U.S. Pat. No. 5,118,793, incorporated by reference.

Alternatively, the amine containing species may be on a solid surface, such as polyethylene, polypropylene, cellulose, nitrocellulose, nylon, glass, glass fibers, plastic, diatomaceous earth, ceramics, metals, polycarbonate, polyurethane, polyester and the like. The surface may be a porous or semiporous matrix, a gel or a viscous liquid such as, for example, commonly found in chromatographic support media such as agarose, sepharose gels, beads and the like. Such supports with glycosaminoglycans, particularly heparin and its analogs, conjugated thereto are useful in a variety of applications such as affinity chromatography, bioseparations and solid phase binding assays. In particular, the use of heparin functional supports to purify antithrombin III is known and reported in U.S. Pat. No. 3,842,061, incorporated by reference. Numerous such amine containing solid supports and methods of derivatizing such supports to incorporate reactive amino groups therein are known to one of skill in the art. Thus, direct covalent conjugates of the terminal aldose residue of a glycosaminoglycan and any species, either known to exist presently or that may be available in the future, containing a reactive amino group are within the scope of this invention.

The methods of the present invention provide glycosaminoglycan conjugates with maximal retention of biological activity. In particular, conjugates of heparin or dermatan sulfate with either ATIII or HCII are provided which possess >60%, typically >90, more typically >95%, and most typically ≧98% of intact unconjugated heparin antithrombin activity. These conjugates have a bimolecular rate constant for thrombin inhibition of 5 to 100 fold higher, generally 8 to 20 fold higher, and typically almost 10 fold higher than the covalent conjugates reported by Collen.

The method of the present invention provides intact heparin molecules conjugated to antithrombin III or heparin cofactor II. Thus, loss of biological activity associated with fragmentation or other modification of heparin prior to conjugation is avoided. It will be apparent to one of skill in the art that the heparin conjugates of this invention retain their anticoagulant activity because of their preparation from intact heparin. Therefore, it is readily apparent that one may use the methods disclosed herein to prepare active heparin conjugates, by first attaching linking groups and spacers to the species sought to be conjugated to heparin (or whatever the glycosaminoglycan being used) and subsequently attaching it to heparin. Numerous methods of incorporating reactive amino groups into other molecules and solid supports are described in the ImmunoTechnology Catalog and Handbook, Pierce Chemical Company (1990), incorporated by reference. Thereby, any species possessing reactive amino groups or capable of being modified to contain such amino groups, by any method presently known or that becomes known in the future, may be covalently conjugated to glycosaminoglycans, such as heparin, by the methods disclosed herein and all such conjugates are contemplated by this invention.

As described above, the present invention takes advantage of the fact that native (isolated from intestinal mucosa) heparin, as well as dermatan sulfate, already contains molecules with aldose termini which would exist as an equilibrium between hemiacetal and aldehyde forms, a fact apparently unrecognized and unexploited in the art. Thus, we have conjugated heparin or dermatan sulfate to antithrombin serpins by reduction of the single, Schiff base formed spontaneously between the aldose terminus aldehyde on heparin or dermatan sulfate and a lysyl amino on the serpin. The heparin or dermatan sulfate is unmodified (unreduced in activities) prior to conjugation and is linked at one specific site at one end of the molecule without any unblocked activation groups or crosslinking of the serpin. Heparin has been covalently linked to ATIII or HCII and dermatan sulfate has been covalently linked to HCII. Conjugation of other GAGs (such as heparan sulfate) to serpins or other proteins (such as albumin) is possible by this method. For example, dermatan sulfate has been conjugated to albumin using the methods disclosed herein.

In another aspect of this invention we have also produced covalent complexes by simply mixing heparin and ATIII in buffer and allowing a keto-amine to spontaneously form by an Amadori rearrangement between the heparin aldose terminus and an ATIII lysyl amino group. Thus, this invention provides methods of using the Amadori rearrangement to prepare conjugates of glycosaminoglycans to amine containing species, particularly proteins. This is a particularly mild and simple method of conjugation, hitherto unrecognized in the art for conjugating such molecules, which minimizes the modification of the glycosaminoglycan, thus maximizing the retention of its biological activity.

Another aspect of this invention provides covalent conjugates of glycosaminoglycans, particularly of heparin, end-labelled with an amine containing species at the terminal aldose residue of the glycosaminoglycan. For example, heparin and ATIII are linked directly together so that the active pentasaccharide sequence for ATIII on the heparin is in close proximity for binding. This is one of the fundamental reasons for making a covalent heparin-ATIII complex, as heparin accelerates inhibition through ATIII only if ATIII can bind the active sequence. Typically, one amine containing species will be attached to each glycosaminoglycan. However, it will be apparent that the ratio of amine containing species to glycosaminoglycan may be reduced below one by adjusting the molar ratios of the reactants or the time of the reaction.

Glycosaminoglycans are available in a variety of forms and molecular weights. For example, heparin is a mucopolysaccharide, isolated from pig intestine or bovine lung and is heterogenous with respect to molecular size and chemical structure. It consists primarily of (1–4) linked 2-amino-2-deoxy-α-D-glucopyroanosyl, and α-L-idopyranosyluronic acid residues with a relatively small amount of β-D-glucopyranosyluronic acid residues. It contains material with a molecular weight ranging from about 6,000 to about 30,000. The hydroxyl and amine groups are derivatized to varying degrees by sulfation and acetylation. Though this invention has been illustrated primarily with respect to heparin, it is apparent that all glycosaminoglycans, irrespective of their molecular weight and derivatization, may be conjugated by the methods disclosed herein, provided they possess a terminal aldose residue. Conjugates of all such glycosaminoglycans and their preparation by the methods disclosed herein are within the scope of this invention. For example, conjugates of heparin derivatized with phosphates, sulfonates and the like as well as glycosaminoglycans with molecular weights less than 6,000 or greater than 30,000 are within the scope of this invention.

In clinical practice, the novel heparin conjugates of the present invention may be used generally in the same manner and in the same form of pharmaceutical preparation as commercially available heparin for clinical use. Thus, the novel heparin conjugates provided by the present invention may be incorporated into aqueous solutions for injection (intravenous, subcutaneous and the like) or intravenous infusion or into ointment preparations for administration via the skin and mucous membranes. One skilled in the art will recognize that all forms of therapy, both prophylactic and curative, either currently known or available in the future, for which heparin therapy is indicated may be practiced with the novel heparin conjugates provided by this invention.

The heparin conjugates of this invention find particular utility in the treatment of neonatal and adult respiratory distress syndrome (RDS). In contrast to the use of noncovalent heparin-ATIII complexes, the use of the covalent heparin conjugates of the present invention prevents loss of heparin in the lung space by dissociation from ATIII. In this case, a solution of covalent complex in a physiologic buffer could be delivered as an atomized spray down the airway into the lung via a catheter or puffer. Long term use in the circulation could be carried out by either intravenous or subcutaneous injection of the complex in a physiologic buffer. The covalent conjugates of this invention may also be used in the treatment of acquired ATIII deficient states characterized by thrombotic complications such as cardiopulmonary bypass, extracorporeal molecular oxygenation, etc. because a longer ½ life of the covalent complex would mean fewer treatments and less monitoring. Additionally, this invention provides for prophylactic treatment of adult patients at risk for deep vein thrombosis.

Premature infants have a high incidence of respiratory distress syndrome (RDS), a severe lung disease requiring treatment with assisted ventilation. Long term assisted ventilation leads to the onset of bronchopulmonary dysplasia (BPD) as a result of lung injury which allows plasma coagulation proteins to move into the alveolar spaces of the lung. This results in the generation of thrombin and subsequently fibrin. The widespread presence of fibrin within the lung tissue and airspaces is consistently observed in infants dying of RDS. This fibrin gel within the airspace impairs fluid transport out of the lung airspaces resulting in persistent and worsening pulmonary edema. This invention provides novel therapies for the treatment of such fibrin-mediated diseases in lung tissue by preventing intra-alveolar fibrin formation by maintaining an "anti-thrombotic environment" and/or enhancing fibrinolysis within lung tissue, thereby decreasing the fibrin load to the air spaces of the lung.

The heparin conjugates will be delivered directly to the airspaces of the lung via the airway prophylactically (before the baby takes its first breath). This ensures that the antithrombotic agent is available directly at the site of potential fibrin deposition and that the bleeding risk associated with systemic antithrombotic therapies is avoided. In addition, the antithrombotic agent will already be present in the lung prior to the start of the ventilatory support which is associated with the initial injury, i.e., unlike systemic antithrombin administration where crossing of the administered drug to the lung airspace does not occur until after lung injury. Since heparin is covalently attached to ATIII it will remain in the lung airspaces. It can also be an adjunctive therapy to the surfactants currently administered to prevent RDS and BPD. By "lung surfactant" is meant the soap-like substance normally present in the lung's airspaces whose main role is to prevent collapse of the airspace. The conjugates can also be delivered repeatedly via the endotracheal tube or as an inhaled aerosol. Adjunctive therapy can also be practiced with asthma medications by inhaler (e.g., anti-inflammatory steroids such as beclomethasone dipropionate), other anti-asthmatics such as cromolyn sodium (disodium salt of 1,3-bis(2-carboxychromon-5-yloxy)-2-hydroxypropane, INTAL®) and bronchodilators such as albuterol sulfate.

A variety of other diseases associated with elevated thrombin activity and/or fibrin deposition can be treated by administration of the conjugates of this invention. The inflammatory processes involved in adult respiratory distress syndrome are fundamentally similar to neonatal RDS and can be treated by the antithrombotic therapy described. Spontaneous lung fibrosis has also been shown to have activation of the coagulation/fibrinolytic cascades in the lung airspaces. Fibrotic disease of the lung is often a side effect associated with cancer chemotherapy and the RDS antithrombotic administration of the covalent heparin conjugates of this invention can be administered prophylactically prior to cancer chemotherapy to prevent lung fibrosis. Administration is repeated after chemotherapy in order to ensure no fibrin formation. A decrease in antithrombin III activity and an increase in thrombin activity in sepsis is also well documented. Sepsis is the most common risk factor for developing adult RDS. Thus, the heparin conjugates of this invention can be used to reduce the mortality associated with septic shock.

The conjugates of this invention are administered at a therapeutically effective dosage, i.e., that amount which, when administered to a mammal in need thereof, is sufficient to effect treatment, as described above (for example, to reduce or otherwise treat thrombosis in the mammal, or to inactivate clot-bound thrombin, or to inhibit thrombus accretion). Administration of the active compounds and salts described herein can be via any of the accepted modes of administration for agents that serve similar utilities.

The level of the drug in a formulation can vary within the full range employed by those skilled in the art, e.g., from about 0.01 percent weight (% w) to about 99.99% w of the drug based on the total formulation and about 0.01% w to 99.99% w excipient. Preferably the drug is present at a level of about 10% w to about 70% w.

Generally, an acceptable daily dose is of about 0.001 to 50 mg per kilogram body weight of the recipient per day, preferably about 0.05 to 25 mg per kilogram body weight per day, and most preferably about 0.01 to 10 mg per kilogram body weight per day. Thus, for administration to a 70 kg person, the dosage range would be about 0.07 mg to 3.5 g per day, preferably about 3.5 mg to 1.75 g per day, and most preferably about 0.7 mg to 0.7 g per day depending upon the individuals and disease state being treated. Such use optimization is well within the ambit of those of ordinary skill in the art.

Administration can be-via any accepted systemic or local route, for example, via parenteral, intravenous, nasal, bronchial inhalation (i.e., aerosol formulation), transdermal or topical routes, in the form of solid, semi-solid or liquid dosage forms, such as for example, tablets, suppositories, pills, capsules, powders, solutions, suspensions, aerosols, emulsions or the like, preferably in unit dosage forms suitable for simple administration of precise dosages. Administration by intravenous or subcutaneous infusion is usually preferred. Most usually, aqueous formulations will be used. The conjugate is formulated in a non-toxic, inert, pharmaceutically acceptable carrier medium, preferably at a pH of about 3–8, more preferably at a pH of about 6–8. Generally, the aqueous formulation will be compatible with the culture or perfusion medium. The compositions will include a conventional pharmaceutical carrier or excipient and a conjugate of the glycosaminoglycan, and in addition, may include other medicinal agents, pharmaceutical agents, carriers, adjuvants, etc. Carriers can be selected from the various oils, including those of petroleum, animal, vegetable or synthetic origin, for example, peanut oil, soybean oil, mineral oil, sesame oil, and the like. Water, saline, aqueous dextrose or mannitol, and glycols are preferred liquid carriers, particularly for injectable solutions. Suitable pharmaceutical carriers include starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol, and the like. Other suitable pharmaceutical carriers and their formulations are described in *Remington's Pharmaceutical Sciences* by E. W. Martin (1985).

If desired, the pharmaceutical composition to be administered may also contain minor amounts of non-toxic auxiliary substances such as wetting or emulsifying agents, pH buffering agents and the like, such as for example, sodium acetate, sorbitan monolaurate, triethanolamine oleate, etc.

The compounds of this invention are generally administered as a pharmaceutical composition which comprises a pharmaceutical excipient in combination with a conjugate of the glycosaminoglycan. The level of the conjugate in a formulation can vary within the full range employed by those skilled in the art, e.g., from about 0.01 percent weight (% w) to about 99.99% w of the drug based on the total formulation and about .01% w to 99.99% w excipient. Preferably, the formulation will be about 3.5 to 60% by weight of the pharmaceutically active compound, with the rest being suitable pharmaceutical excipients.

The following examples are given to enable those of skill in the art to more clearly understand and practice the invention. They should not be considered as limiting the scope of the invention, but merely illustrative and representative thereof.

Materials

Heparin was from porcine intestinal mucosa (Sigma Chem Co U.S.A.). Dermatan sulfate was from porcine intestinal mucosa (Mediolanum farmaceutici S.p.A., Italy). ATIII was from human plasma (Bayer Inc.) HCII was from human plasma (Affinity Biologicals).

EXAMPLE I

Preparation of Covalent Conjugates between GAGs and Serpins

Reactions to form covalent complexes between the glycosaminoglycan (GAG) and serpin, for example ATIII or HCII, involved incubation of GAG (5 mg–70 mg) with the serpin (0.5 mg–3 mg) in 1 mL of sterile filtered buffer (0.3M phosphate 1M NaCl, pH 8.0 or 0.02M phosphate 0.15M NaCl, pH 7.3) containing 0.05M sodium cyanoborohydride at 35° C. to 45° C., preferably 40° C., in a sealed plastic tube (polycarbonate, polypropylene, etc). omitting the sodium cyanoborohydride allowed formation of covalent complexes via Amadori rearrangement which could be radiolabeled by later addition of tritium labelled sodium borohydride. Incubation times ranged from 3 days to 2 weeks. Purification of the covalent product was achieved by a variety of methods. Purification procedures are described in U.S. Pat. No. 5,308, 617, U.S. Pat. No. 4,623,718 and FEBS Letters 143(1) :96–100, 1982, all incorporated by reference. Gel filtration on Sephadex G-200 using 2M NaCl produced a high molar mass fraction containing covalent complex that was essentially void of free serpin. This fraction was further purified by electrophoresis on a 7.5% polyacrylamide gel at pH 8.8 using nondenaturing conditions (no sodium dodecyl sulfate), cutting out the section of gel containing only complex and elution of the product from the cut up section of gel by incubation in buffer (3.0 g/L tris (hydroxymethyl) aminomethane 14.4 g/L glycine pH8.8) at 23 degrees C.

Alternatively, the antithrombin-heparin conjugate (ATH) was also purified in one step from the reaction mixture by hydrophobic chromatography on butyl-agarose (Sigma Chemical Company, Milwaukee, Wis.). In 2.5M ammonium sulfate, ATH and ATIII bound to butyl-agarose beads while heparin did not. Adjusting the ammonium sulfate concentration from 2.5M to 1.8M allowed pure ATH to be eluted from the beads while ATIII remained bound.

Also, ATH and ATIII bound to butyl-agarose could be eluted together by adjusting the ammonium sulfate concentration to less than 1.5M followed by separation of the ATH from ATIII on DEAE Sepharose Fast Flow beads (Pharmacia Biotech, Uppsala Sweden). ATH and ATIII eluted from butyl-agarose were dialyzed versus 0.01M Tris-HCl pH 8.0 buffer prior to binding to the DEAE beads and the bound ATIII eluted with 0.2M NaCl in buffer while ATH was eluted by NaCl concentrations of 0.4M to 2.0M. In this way, ATH of different molecular weights and charges could be isolated, depending on the NaCl concentration used. Concentration of the purified ATH was done at 4° C. by dialysis in tubing, with a 12000–14000 molar mass cut off, under nitrogen pressure (1 atmosphere).

ATH produced in 0.02M phosphate, 0.15M NaCl, 0.05M sodium cyanoborohydride pH 7.3 and purified using elution of the complex from a cut out section of gel following nondenaturing electrophoresis, yielded material in which the molar ratio of ATIII:H in the complex was 1:1.1 and >99% was active.

EXAMPLE II

Characterization of GAG-Serpin Coniuqates

1. Structural Characterization

The procedure to determine the molar ratio of Hep:AT in the heparin-antithrombin conjugates (ATH) was by densitometry of SDS gels (standard procedures) stained for either heparin (alcian blue/silver) or ATIII (Coomassie blue) compared with the corresponding standards. The activating groups per GAG molecule is by definition 1 (one aldose terminus per GAG chain).

The molecular weight range was determined from comparison of stained ATH, HCH, HCD with prestained standards on SDS polyacrylamide gels.

Characteristics of antithrombin-heparin conjugates(ATH) and heparin cofactor II-heparin (HCH) and heparin cofactor II-dermatan sulfate (HCD) conjugates are shown below in Table I.

TABLE I

CHARACTERISTICS OF COVALENT ATH PRODUCTS

| PRODUCT | MOLAR RATIO HEP:AT | ACTIVATING GROUPS PER HEP | MOL. WT. (SDS PAGE) | ANTI-Xa* | ANTI-IIa* |
|---|---|---|---|---|---|
| BERRY et al. | 1.1 | 1 | 69 kD– 100 kD | | >98% |
| COLLEN et al. | 0.8–0.9 | 2.1 | | 65% | ≦65% |
| BJORK et al. | 0.7 | 1 | | 82% | UNDETECTABLE |

*ACTIVITY OF HEPARIN IN COMPLEX COMPARED TO UNMODIFIED STARTING HEPARIN

CHARACTERISTICS OF COVALENT HCH AND HCD PRODUCTS

| PRODUCT | MOLAR RATIO GAG:AT | ACTIVATING GROUPS PER GAG | MOL. WT. (SDS PAGE) | ANTI IIa* |
|---|---|---|---|---|
| HCH | 1.1 | 1 | 70 kD–115 kD | >90% |
| HCD | 1.4 | 1 | 78 kD–150 kD | >90% |

*PERCENT OF MOLECULES ACTIVE AGAINST IIa

2. Biological Activity

Anti-Xa activity measured by Collen et al. and Bjork et al. for their respective ATH preparations was carried out by (pre)incubation of the ATH with Xa followed by determination of residual activity of Xa with S-2222 (N-benzoyl-isoleucyl-glutamyl-glycyl-arginyl-paranitroanilide (from Chromogenix, Sweden)). The percent of ATH molecules with activity (as determined by amount of Xa inhibited) is reported in Table I. Anti-IIa activity was measured for our ATH by titration with different amounts of IIa (thrombin). The amount of IIa inhibited by a given mass concentration of ATH (mass determined by analysis using unmodified starting heparin) was determined by measuring residual activity against S-2238 (D-phenylalanyl-pipecolyl-arginyl-paranitroanilide (from Chromogenix, Sweden)).

Inhibition of Thrombin Activity

Figure 1:
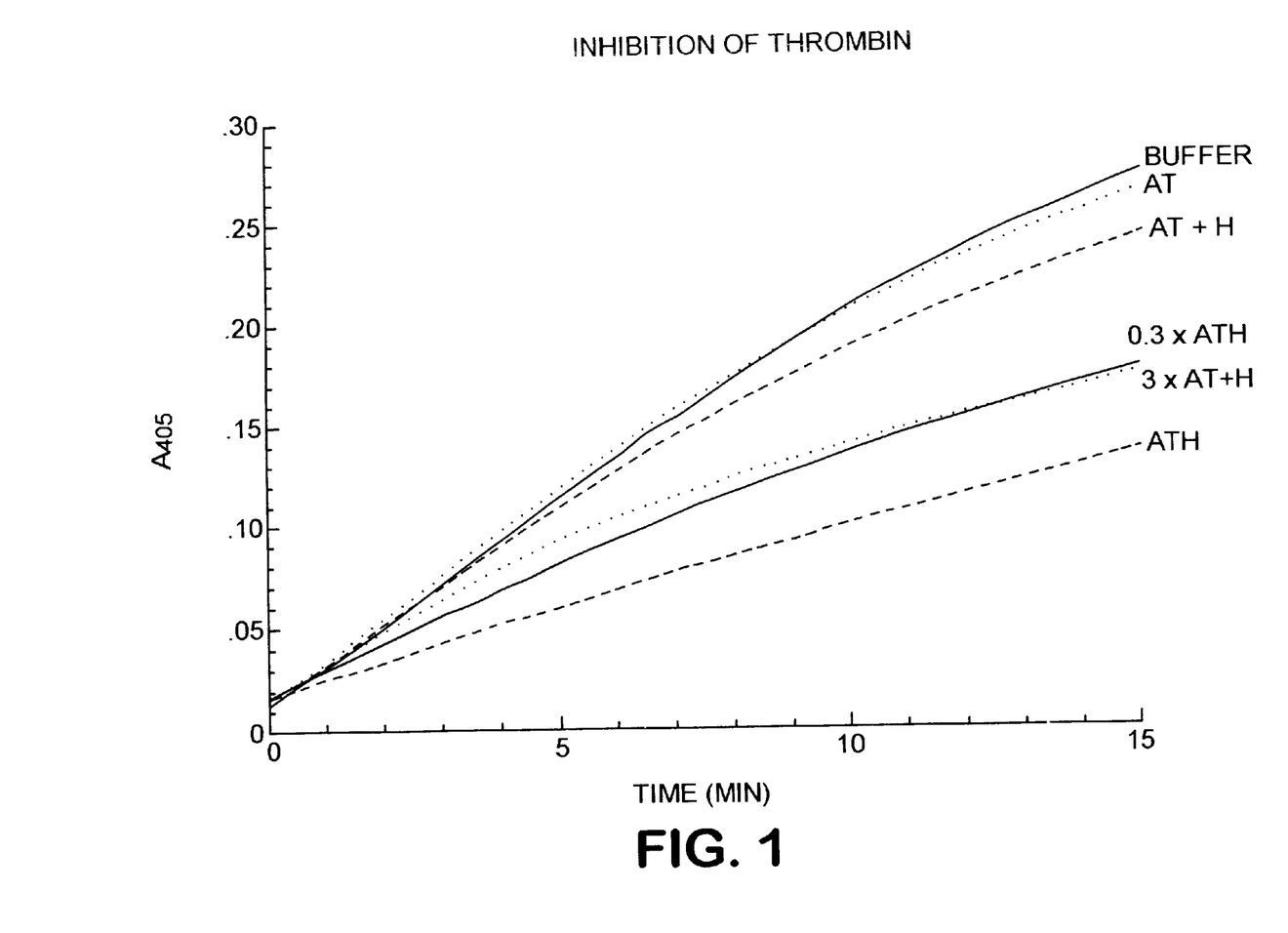
FIG. 1 compares the inhibition of thrombin activity by antithrombin III, noncovalent antithrombin III-heparin complexes and various concentrations of the covalent antithrombin III-heparin (ATH) conjugates of the present invention.

The inhibition of the reaction of bovine thrombin with the chromogenic substrate S-2238 was studied. All operations were carried out at 23° C. Thrombin was added, with mixing, to a solution containing the material to be tested and S-2238 dissolved in 0.036M sodium acetate 0.036M sodium barbital, 0.145M NaCl pH 7.4 buffer in an eppendorf tube (the final thrombin concentration was 0.045 I.U./ml and the final S-2238 concentration was 28.3 µg/ml). The resultant solution was transferred to a quartz cuvette and absorbance readings at 405 nm taken over time (zero time being 30 sec after addition of the thrombin). The reaction concentration of the ATIII in either the ATH, ATIII or ATIII+H (heparin) reactions was 8.8 nM. The [ATIII] in the 0.3×ATH and 3×AT+H reactions was 2.7 nM and 27 nM, respectively. In reactions where heparin was used, it was present in equimolar concentrations to the ATIII in that experiment. The results are shown in FIG. 1 and show that the ATH conjugates of the present invention are more effective than free ATIII and heparin.

Thrombin was from Parke-Davis. S-2238 was from Chromogenix (Sweden). Standard Heparin (Leo Laboratories) was used.

Reaction with Fibrinogen and Thrombin

Figure 2:
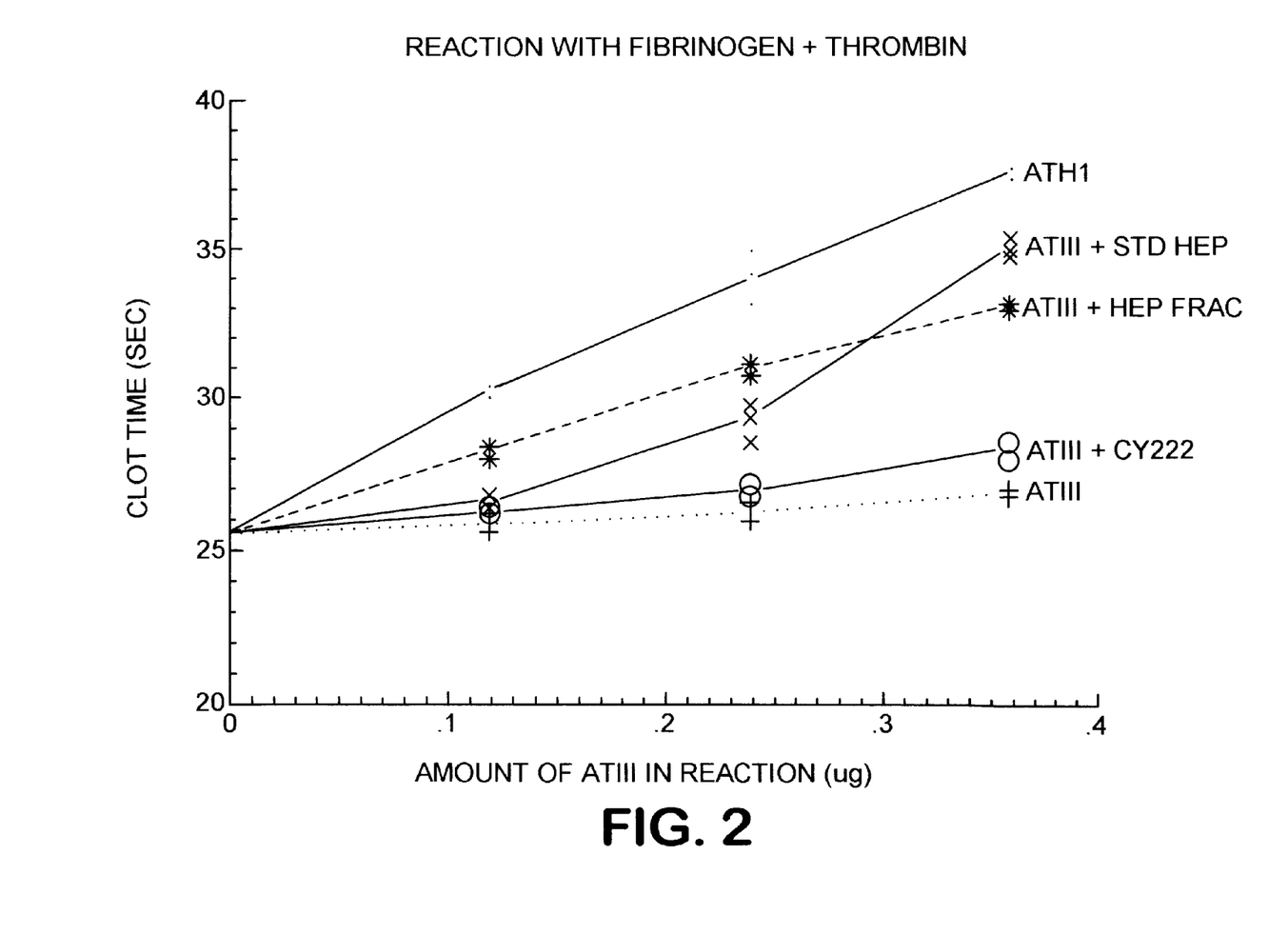
FIG. 2 shows the inhibition of the ability of thrombin to clot human fibrinogen by the covalent antithrombin III-heparin conjugates (ATH1) of the present invention.

The ability of bovine thrombin to clot human fibrinogen was inhibited by various ATIII containing mixtures as follows. An ATIII containing sample was mixed with fibrinogen in 0.15M NaCl in a plastic tube at 37° C. After 1 min, thrombin was added (the final fibrinogen concentration was 0.2 mg/ml and the final thrombin concentration was 1 I.U./ml) and a clock was started. The time was recorded for the first appearance of a clot on the end of a nichrome wire loop used for agitation. The results are shown in FIG. 2 and show that the ATH conjugates are more effective at preventing clotting. The following abbreviations are used.

ATH1=preparation #1 of ATIII-Heparin conjugate(as described in Example 1)
STD Hep=standard heparin (LEO laboratories)
HEP FRAC=low molecular weight fraction (≈7000 MW, produced by gel filtration) of standard heparin
CY222=low molecular weight heparin fragment produced by nitrous acid (average ≈2500 MW, produced by Choay Laboratories)

Thrombin was from Parke-Davis; Fibrinogen was from Connaught Laboratories. ATIII was purified from human plasma. In ATIII +heparin mixtures, the protein and GAG content were equivalent on a mass basis (only 1 in 3 standard heparin molecules bind ATIII).

Effect of Added Heparin on Rate of Inhibition of Thrombin Activity by Covalent ATIII-Heparin Conjuqates (ATH)

Figure 3:
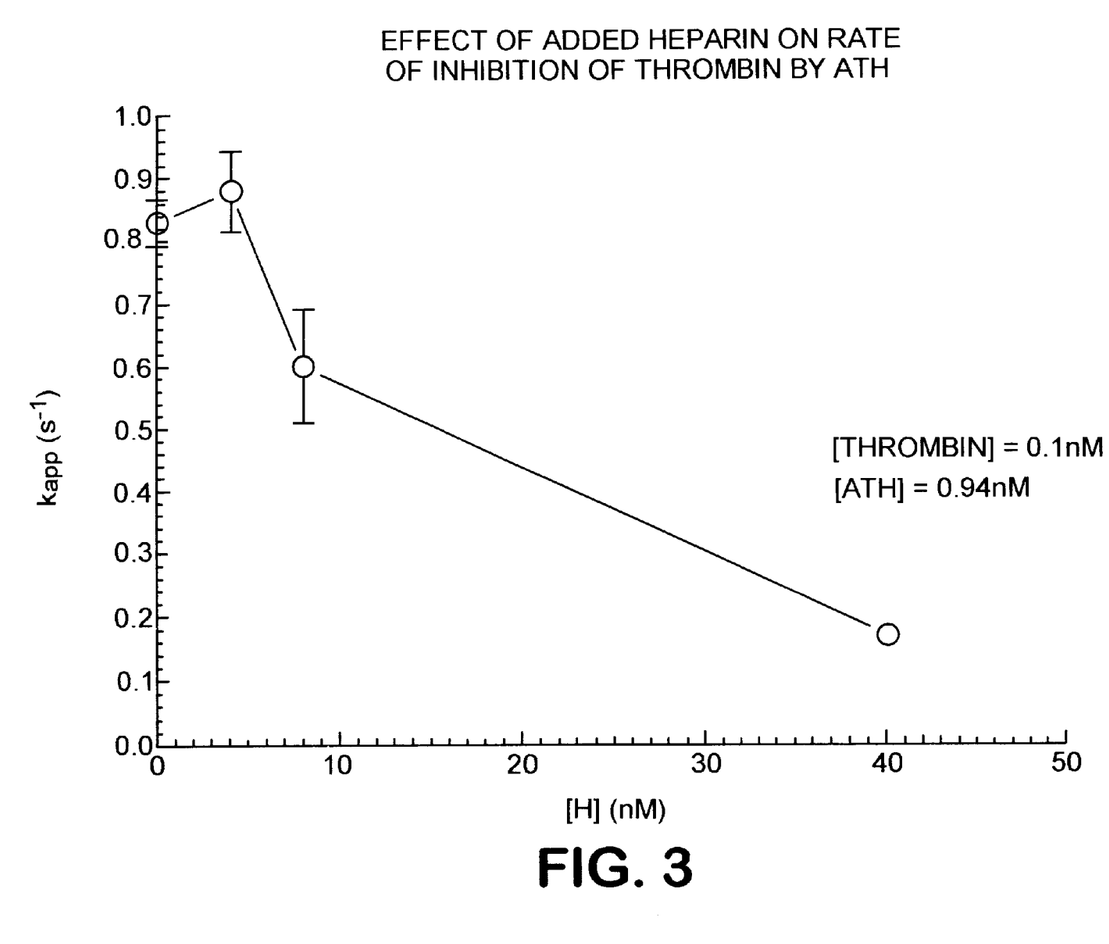
FIG. 3 shows the effect of added heparin on the rate of inhibition of thrombin by the antithrombin III-heparin conjugates of the present invention.

The ability of standard heparin to affect the inhibition of the human thrombin by ATH was tested. The buffer used was 0.1M Tris-HCl, 0.15M NaCl, 1.5 μM bovine albumin pH 7.6. ATH and varying amounts of heparin in buffer were placed in a 8 mm diameter, flat bottomed, polycarbonate, plastic tube equipped with a stirring bar rotating at 500–1000 rpm, all in a 37° C. water bath. Human thrombin was added immediately as a clock was started. After a time ranging from 0.5 to 5 sec, thrombin inhibition was stopped by addition of a solution of excess polybrene and S-2238. Residual thrombin activity for S-2238 ($A_{405}$/min) was measured in a quartz cuvette at 37° C. The results are shown in FIG. 3. A semi-log plot of residual thrombin activity (Log ($A_{405} \times 10^4$/min)) versus time (sec) was constructed for each heparin concentration used. The apparent rate constant ($k_{app}$ ($S^{-1}$)) was calculated as 1 n 2 divided by the time at which ½ of the starting thrombin activity was inhibited. The $k_{app}$ for each heparin concentration is plotted.

Bovine albumin was from Sigma Chemical Company, Human thrombin was from Enzyme Research Laboratories (U.S.A.), S-2238 was from Chromogenix (Sweden) and heparin was from Leo Laboratories, Canada. All concentrations quoted on FIG. 3 are reaction concentrations just prior to polybrene-S-2388 addition.

Determination of Rates of Thrombin Inhibition by ATH

Figure 4:
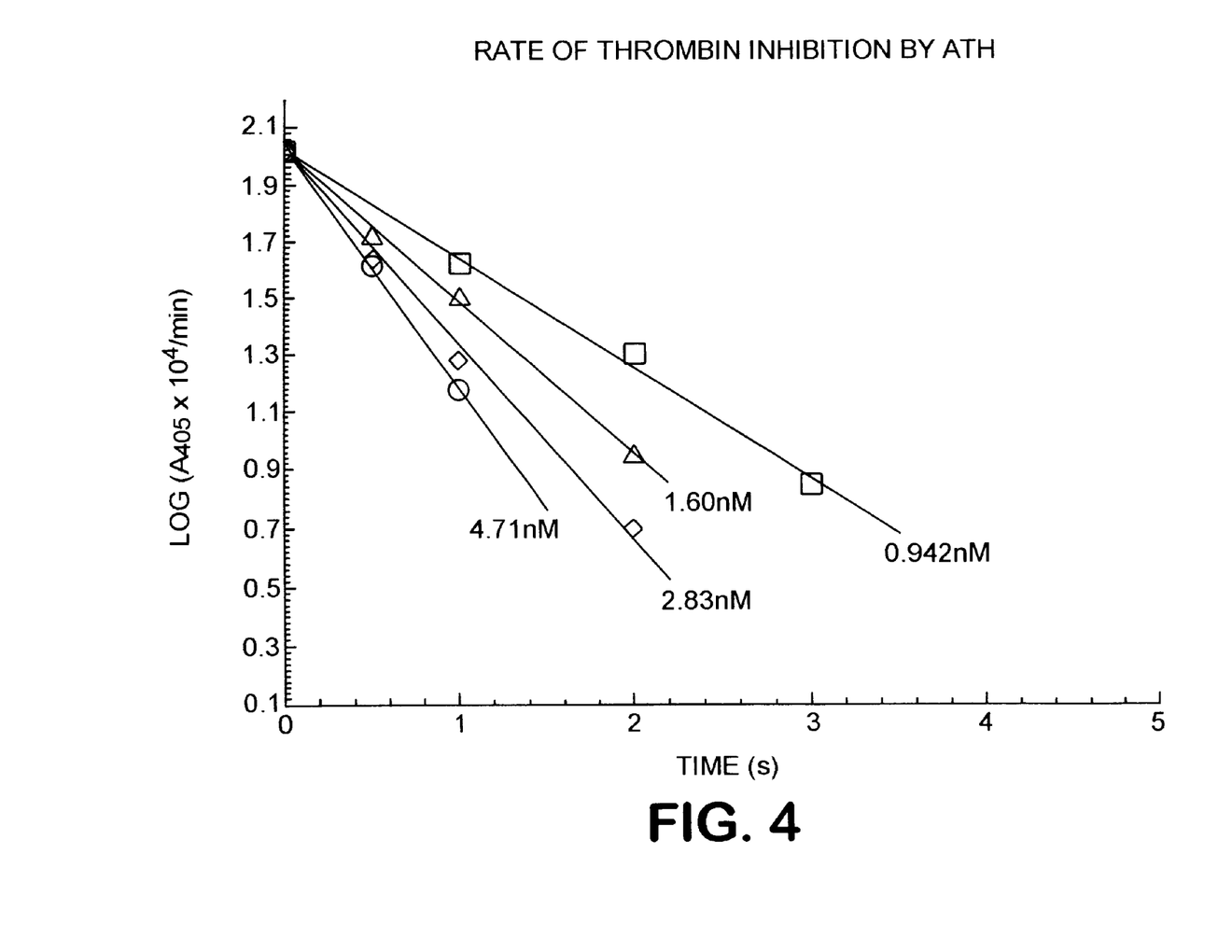
FIG. 4 shows the rate of inhibition of thrombin activity towards the chromogenic substrate S-2238 by the antithrombin III-heparin conjugates of the present invention.

The experimental procedure and calculation of the semi-log plot was the same as the experiments described above for FIG. 3 except that no exogenous heparin was added and the concentration of ATH was varied as shown. The results are shown in FIG. 4.

Inhibition of Thrombin+ATH Reaction by FPR-Thrombin

Figure 5:
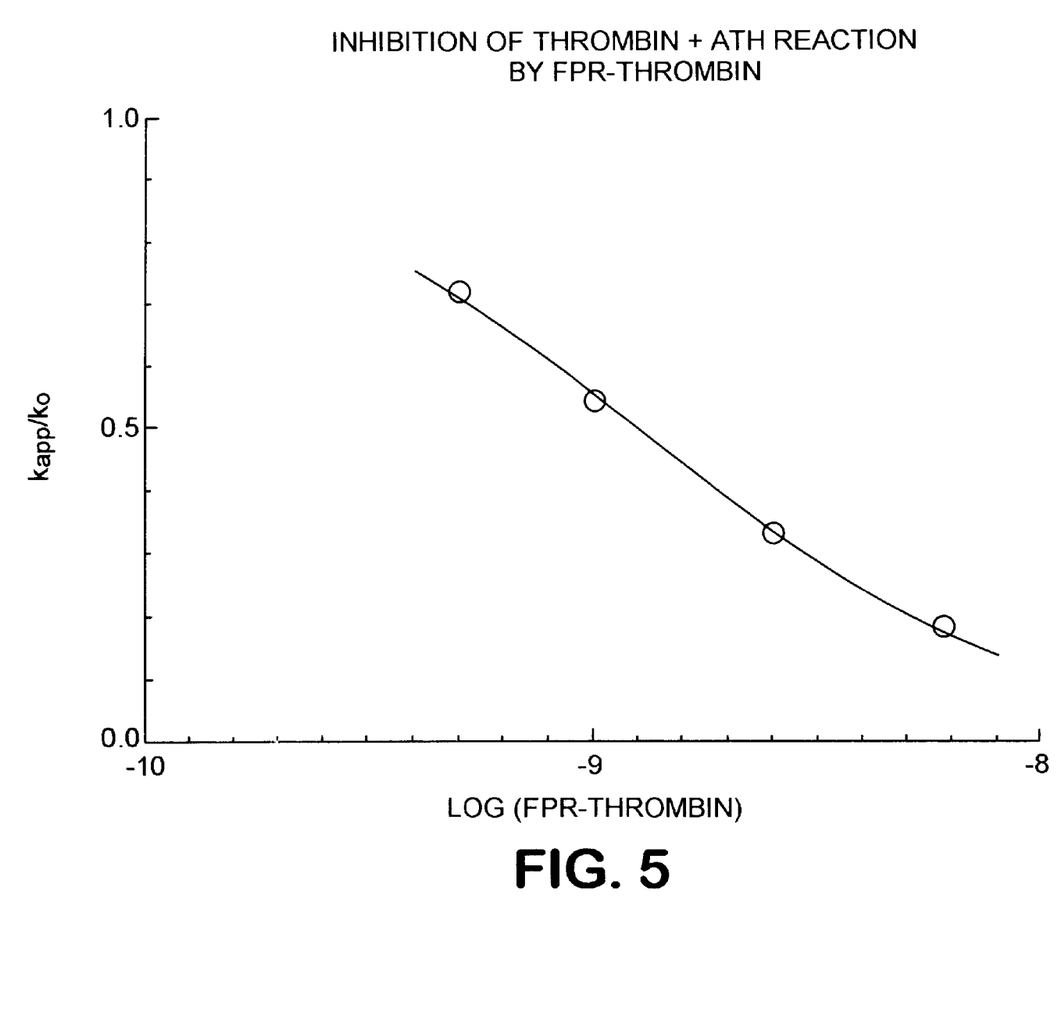
FIG. 5 shows the inhibition of the antithrombotic effect of the covalent ATH conjugates of the present invention by FPR-thrombin.

FPR-thrombin is thrombin inhibited by phenylalanyl-prolyl-arginyl peptide covalently bonded to its active serine. FPR-thrombin can competitively inhibit the reaction of thrombin with ATH by binding to the heparin chain although it cannot react with the ATIII portion. The experimental procedure and calculation of $k_{app}$ was the same as for the experiments for FIG. 3 except that varying amounts of FPR-thrombin were tested instead of heparin (no exogenous heparin added). The constant $k_o$ was the $k_{app}$ value with no FPR-Thrombin added. Results are shown in FIG. 5.

Bimolecular and 2nd Order Rate Constants and Effect of Added Heparin on Rate of Inhibition of Thrombin by ATH The procedure for the results for added heparin are given as determined from the results used for FIG. 3. To determine the rate constants, the method of Hoylaerts et al. in *J. Biol. Chem.* 259(9):5670–5677 (1984) was used. To calculate the bimolecular rate constant, $k_2$ and $K_i$ were determined as follows. The $k_{app}$ values for each curve for each ATH concentration used were determined for 3 separate experiments, of which FIG. 4 is a typical example. For each experiment, a plot of $1/k_{app}$ versus 1/[ATH] was constructed. The intercept of the $1/k_{app}$ axis was equal to $1/k_2$ and the intercept of the 1/[ATH] axis was equal to $1/K_i$. In each case, the bimolecular rate constant was calculated as $k_2/K_i$ and the average of 3 experiments is reported. For the second order rate constant ($k_1$), $k_{-1}$(off rate), or $IC_{50}$ for FPR-thrombin competition ([FPR-Thrombin] at which $k_{app}/k_0$=0.5) was determined for each curve for each of 3 experiments, of which FIG. 5 is a typical example. The averages, for the three $k_2$ and $K_i$ values measured were used to calculate the second order rate constant for each $k_{-1}$ value, given the following formula. Second order rate constant=$k_1$=($k_{-1}+k_2$)/$K_i$. The average is reported. Results are shown in Table 2. Error values are expressed as ±2 times the standard error of the mean.

TABLE II

| PRODUCT | BIMOLECULAR RATE CONSTANT ($M^{-1}s^{-1}$) | 2nd ORDER RATE CONSTANT ($M^{-1}s^{-1}$) | EFFECT OF >10 FOLD MOLAR EXCESS ADDITION OF HEPARIN |
|---|---|---|---|
| BERRY et al. | $1.3 \times 10^9 \pm 2 \times 10^8$ | $3.1 \times 10^9 \pm 4 \times 10^8$ | INHIBITION OF ANTI-IIa ACTIVITY |
| COLLEN et al. | $3 \times 10^4$ | $6.7 \times 10^8$ | ANTI-Xa ACTIVITY DOUBLED |
| BJORK et al. | — | — | |

Pharmacokinetics of Covalent ATIII-Heparin Conjugates

1. Plasma Clearance of ATH and Heparin After Intravenous Injection in Rabbits

Figure 6:
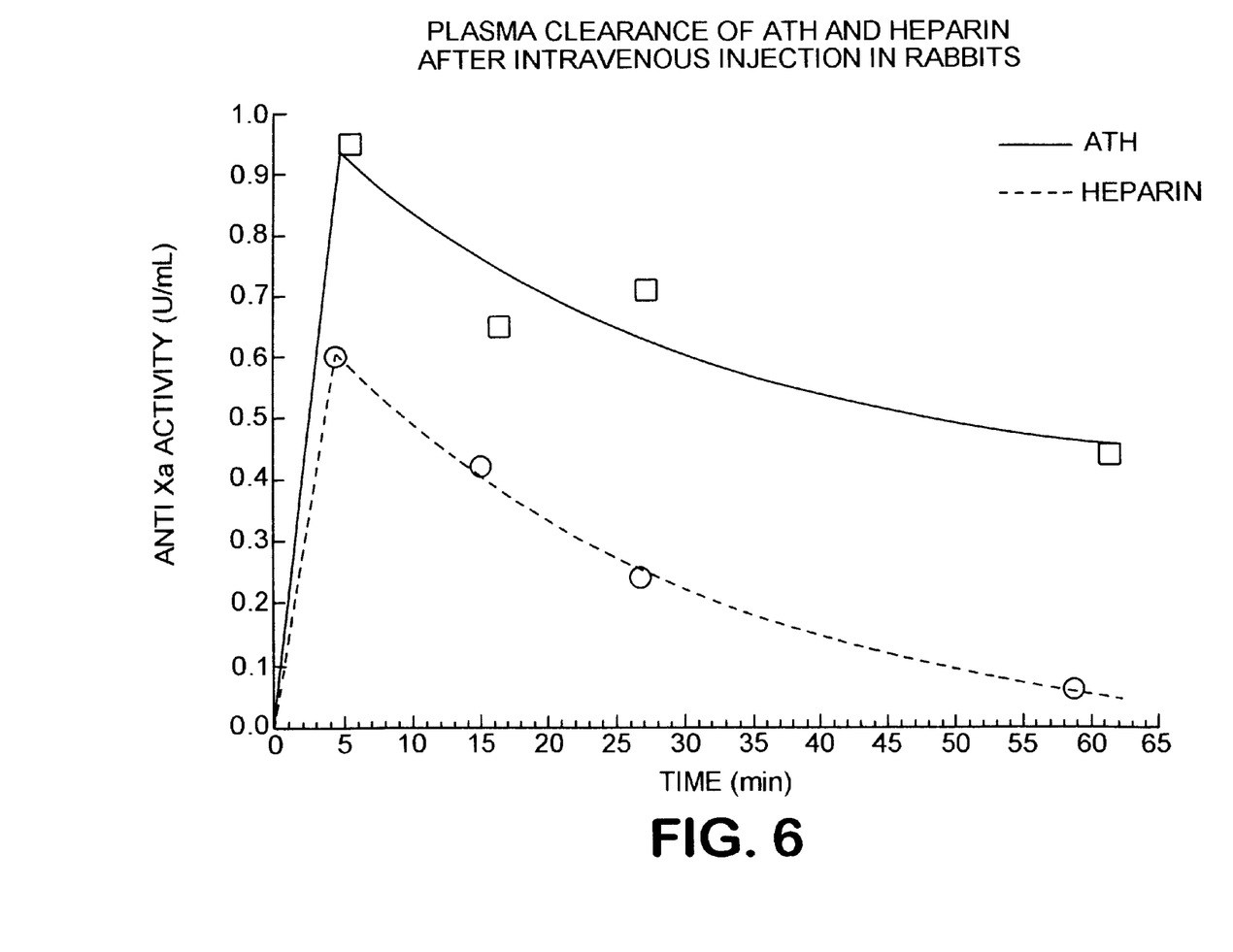
FIG. 6 shows the plasma clearance of the covalent ATH conjugates of the present invention and heparin in rabbits after intravenous injection.
Figure 7:
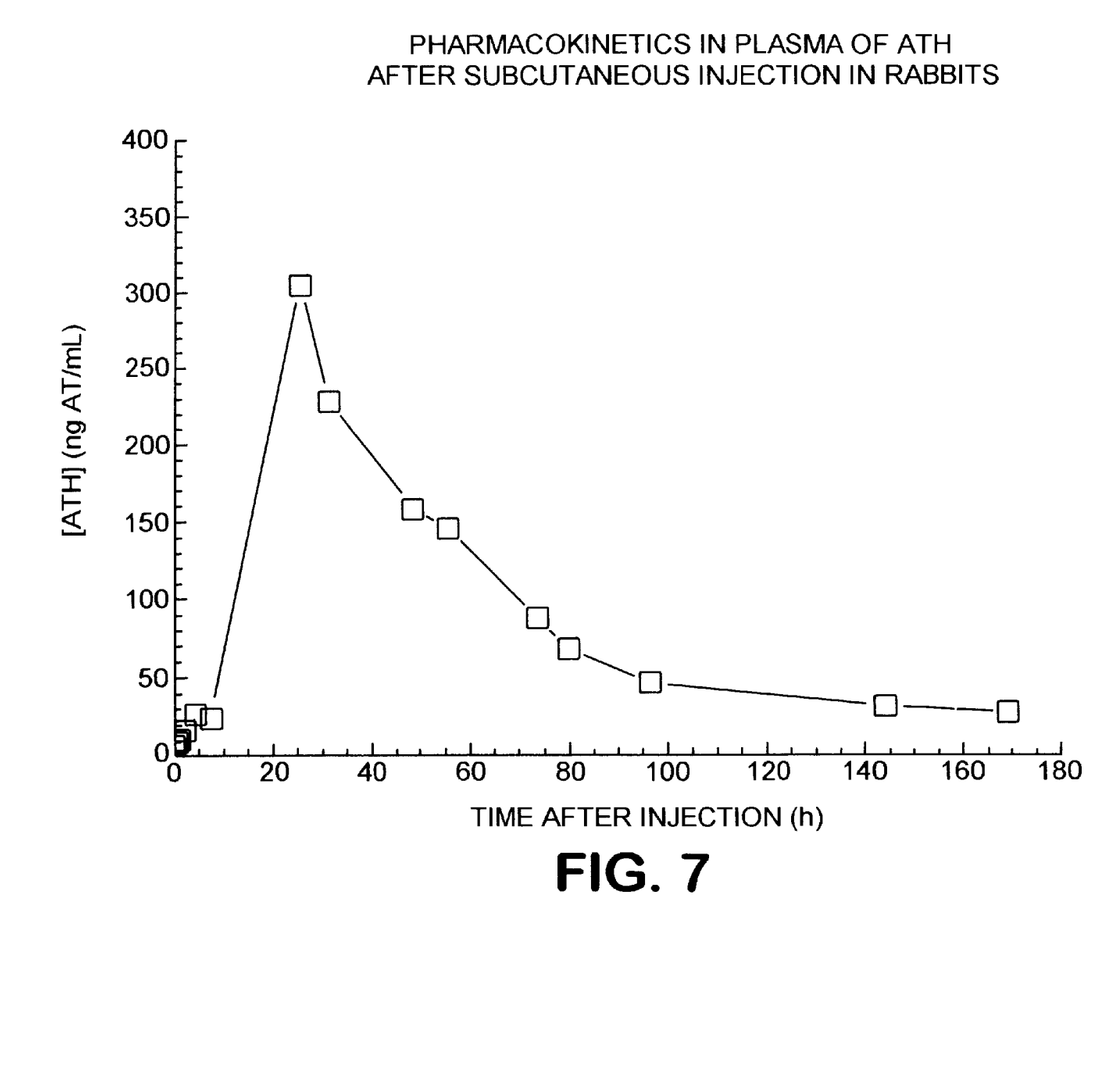
FIG. 7 shows the plasma concentrations of the covalent ATH conjugates of the present invention in rabbits after subcutaneous injection.

Purified ATH and standard heparin (Sigma) were injected into the ear vein of separate rabbits. Equivalent amounts (by mass of heparin) were injected. At various times, blood samples were withdrawn from the ear artery of each rabbit into sodium citrate (9 parts blood to 1 part 3.8% (m/v) trisodium citrate). Each sample was centrifuged at 3000 g and the resultant plasma supernatants analyzed for anti-Xa activity using an ACL300 machine (Coulter U.S.A.) for automation. The procedure employed a Stachrom Heparin kit (Diagnostica Stago, France). Briefly, each sample of plasma to be tested was mixed with buffer containing bovine ATIII and incubated with bovine factor $X_a$ at 37° C. for 30 sec followed by a 30 sec incubation with the chromogenic substrate CBS 31.39 (N-(methylsulfone)-D-leucyl-glycyl-arginyl-paranitroanilide (from Diagnostica Stago, France)), after which reaction was stopped by addition of acetic acid. The absorbance at 405 nm was then measured. A standard curve, generated using standard heparin, was used to determine the anti-$X_a$ activity in the plasma samples in terms of I.U./ml of heparin. Results are shown in FIG. 6. The ATH half life was observed to be 53 minutes and the free heparin half life was observed to be 17 minutes.

2. Pharmacokinetics in Plasma after Subcutaneous Injection in Rabbits

Figure 8:
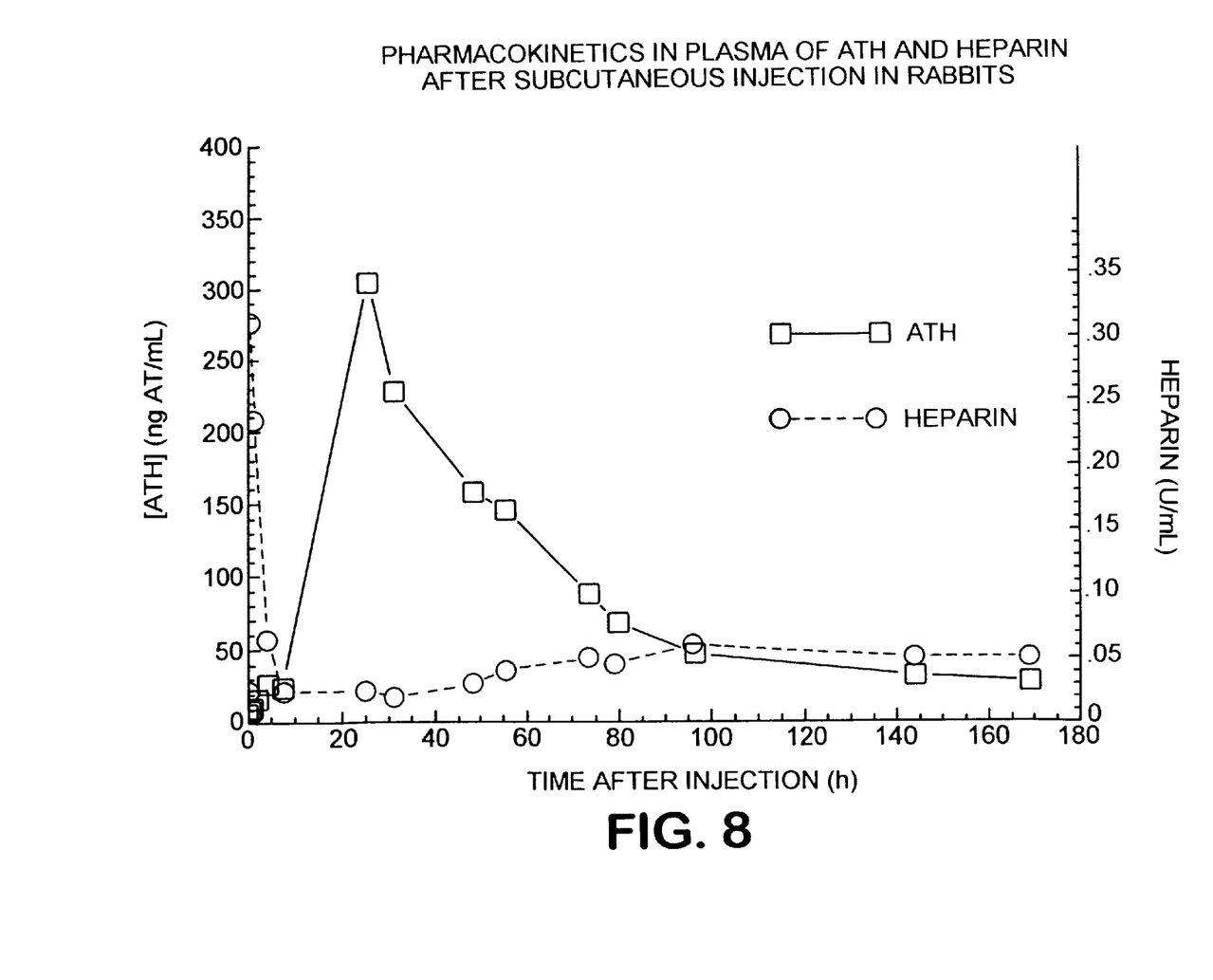
FIG. 8 shows the plasma concentrations of the covalent ATH conjugates of the present invention and heparin in rabbits after subcutaneous injection.

Rabbits were injected under the skin behind the neck and blood sampling for plasma analysis being done at various times as described above for FIG. 6. ATH was detected using an ELISA kit for ATIII from Affinity Biologicals (Hamilton, Canada). Briefly, ATH from sample plasmas was captured on plastic wells coated with sheep anti-human ATIII polyclonal antibodies. Peroxidase conjugated affinity purified anti-human ATIII antibodies (polyclonal) were applied to the wells and, after rinsing, color developed with $H_2O_2$/O-phenylenediamine substrate for 10 min. After terminating substrate reaction with $H_2SO_4$, the absorbance at 490 nm was measured. Standard curves of ATH or human ATIII in pooled normal rabbit plasma were used to determine the ng of human ATIII/ml. The rabbit's own ATIII did not interfere significantly, as the antibody used was selective for human ATIII. Results are shown in FIG. 8. In a separate experiment, when ATIII and heparin (noncovalent conjugate) was injected subcutaneously, ATIII (detected by ELISA) appeared in plasma with the same profile as ATH, but no heparin activity was observed.

All patents, patent applications and publications described herein are incorporated by reference whether specifically incorporated previously or not.

Although the foregoing invention has been described in some detail by way of illustration and example for the purposes of clarity and understanding, it will be obvious that certain changes and modifications may be practiced within the scope of the appended claims.

What is claimed is:

1. A covalent conjugate composition comprising glycosaminoglycans linked by covalent linkages to a species comprising at least one primary amino group, wherein said species is directly covalently linked via said amino group to a terminal aldose residue of said glycosaminoglycans, said covalent linkages comprising an α-carbonyl amine formed by a substantial amount of subsequent Amadori rearrangement of imines resulting from reaction between said amino group and said terminal aldose residue of said glycosaminoglycans, or a pharmaceutically acceptable salt thereof, wherein said glycosaminoglycans are heparin (H) and said amino-containing species is antithrombin III (AT).

2. A covalent conjugate composition comprising glycosaminoglycans and molecules comprising at least one amino group, wherein said amino group is directly linked to said glycosaminoglycans by covalent linkages, wherein said conjugate composition is made by the process comprising:

(a) incubating said glycosaminoglycans with said molecules at a pH and for a time sufficient for imine formation between said amino group and a terminal aldose residue of said glycosaminoglycans, and at a time and temperature sufficient for said imines to undergo a substantial amount of subsequent Amadori rearrangement to an α-carbonyl amine forming said covalent linkages;

(b) isolating said conjugate composition,
or a pharmaceutically acceptable salt thereof,
wherein said glycosaminoglycans are heparin (H) and said amino-containing molecules are antithrombin III (AT).

3. A process for preparing a conjugate composition of molecules comprising at least one primary amino group linked to glycosaminoglycans by covalent bonds, said process comprising:

(a) incubating said glycosaminoglycans with said molecules at a pH and for a time sufficient for formation of an imine between said amino group and a terminal aldose residue of said glycosaminoglycans, and at a time and temperature sufficient for said imines to undergo a substantial amount of subsequent Amadori rearrangement to an α-carbonyl amine forming said covalent bonds; and (b) isolating said conjugate composition,
wherein said glycosaminoglycans are heparin (H) and said amino-containing molecules are antithrombin III (AT).

4. A pharmaceutical preparation, containing a conjugate as in claim 1 as active ingredient in association with a pharmaceutically acceptable carrier.

5. A pharmaceutical preparation as described in claim 4, in the form of an aqueous solution for injection or in the form of an ointment or in the form of an aerosol.

6. The conjugate of claim 1, wherein said covalent linkage comprises a —CO—$CH_2$—NH— group formed by Amadori rearrangement of a —HCOH—HC=N— group resulting from reaction between said amino group and the C1 carbonyl group of said terminal aldose residue.

7. A conjugate composition comprising a substantial amount of glycosaminoglycans covalently bonded to an amino-containing species by —CO—$CH_2$—NH—, said CO—$CH_2$— portion being derived from said glycosaminoglycan and said NH portion being derived from in amino group of said species, wherein said glycosaminoglycans are heparin (H) and said amino-containing species is antithrombin III (AT).

8. A conjugate composition comprising a substantial amount of a complex of the formula: glycosaminoglycan CO—$CH_2$—NH— protein, wherein raid glycosaminoglycan is heparin (H) and said protein is antithrombin III (AT).

9. A pharmaceutical preparation containing a conjugate as in claim 8 as active ingredient in association with a pharmaceutically acceptable carrier.

10. A method of reducing the thrombogenicity of a material comprising coating said material with the conjugate of claim 8.

11. A conjugate of claim 1, wherein the molar ratio of amino-containing species to glycosaminoglycan is less than one.

12. A conjugate of claim 7, wherein the molar ratio of amino-containing species to glycosaminoglycan is less than one.

13. A conjugate of claim 2, wherein the molar ratio of protein to glycosaminoglycan is less than one.

14. A conjugate of claim 8, wherein the molar ratio of protein to glycosaminoglycan is less than one.

15. A conjugate composition of claim 1 wherein said linkages comprise an α-carbonyl amine formed by essentially complete subsequent Amadori rearrangement.

16. A conjugate composition of claim 2 wherein said imine has undergone essentially complete subsequent Amadori rearrangement.

17. A process of claim 3 wherein said imine has undergone essentially complete subsequent Amadori rearrangement.

18. A conjugate composition of claim 7 wherein said substantial amount is essentially all.

19. A conjugate composition of claim 8 wherein said substantial amount is essentially all.

20. An isolated conjugate composition of claim 1.

21. An isolated conjugate composition of claim 2.

22. An isolated conjugate composition of claim 7.

23. An isolated conjugate composition of claim 8.

24. An isolated conjugate composition of claim 18.

25. A pharmaceutical composition comprising a conjugate composition of claim 2 and a pharmaceutically acceptable carrier.

26. A pharmaceutical composition comprising a conjugate composition of claim 7 and a pharmaceutically acceptable carrier.

27. A pharmaceutical composition comprising a conjugate composition of claim 8 and a pharmaceutically acceptable carrier.

28. A pharmaceutical composition comprising a conjugate composition of claims 18 and a pharmaceutically acceptable carrier.

29. A conjugate composition of claim 1 pharmaceutically suitable for injection in a human.

30. A conjugate composition of claim 2 pharmaceutically suitable for injection in a human.

31. A conjugate composition of claim 7 pharmaceutically suitable for injection in a human.

32. A conjugate composition of claim 8 pharmaceutically suitable for injection in a human.

33. A conjugate composition of claim 18 pharmaceutically suitable for injection in a human.

34. A conjugate composition of claim 2 wherein said incubating is carried out from about 3 days to two weeks at a temperature of 35° C. to 45° C.

35. A conjugate composition of claim 34 wherein said incubating is carried out for about 10 days.

36. A conjugate composition of claim 34 wherein said incubating is carried out for about two weeks.

37. A process of claim 3 wherein said incubating is carried out from about 3 days to two weeks at a temperature of 35° C. to 45° C.

38. A process of claim 37 wherein said incubating is carried out for about 10 days.

39. A process of claim wherein said incubating is carried out for about two weeks.

40. A conjugate composition of claim 7 wherein said conjugate has a longer half-life than heparin.

41. A conjugate composition of claim 7, wherein said conjugate is more effective at inhibiting thrombin than are free ATIII and heparin.

42. A conjugate composition of claim 7, wherein said conjugate inactivates clot-bound thrombin.

43. A conjugate composition of claim 7, wherein in said conjugate the molar ratio of heparin to antithrombin is 1:1.

44. A conjugate composition of claim 7, wherein the molecular weight of said conjugate is 69 kD–100 kD.

45. A conjugate composition of claim 7, wherein said conjugate possesses >60% the antithrombin activity of intact unconjugated heparin.

46. A conjugate composition of claim 7, wherein said conjugate possesses >90% the antithrombin activity of intact unconjugated heparin.

47. A conjugate composition of claim 7, wherein said conjugate possesses >95% the antithrombin activity of intact unconjugated heparin.

48. A conjugate composition of claim 7, wherein said conjugate possesses >98% the antithrombin activity of intact unconjugated heparin.

49. A covalent conjugate composition comprising glycosaminoglycans linked by covalent linkages to species comprising at least one primary amino group, wherein said species is directly covalently linked via said amino group to a terminal aldose residue of said glycosaminoglycans, said covalent linkages comprising an α-carbonyl amine formed by a substantial amount of subsequent Amadori rearrangement of imines resulting from reaction between said amino group and said terminal aldose residue of said glycosaminoglycans, or a pharmaceutically acceptable salt thereof, wherein said glycosaminoglycans are heparin (H) and said amino-containing species is antithrombin III (AT), or said glycosaminoglycans are heparin and said amino-containing species is heparin cofactor II, or said glycosaminoglycans are dermatan sulfate and said amino-containing species is heparin cofactor II.

* * * * *